US008712491B2

(12) United States Patent
Evelegh

(10) Patent No.: US 8,712,491 B2
(45) Date of Patent: *Apr. 29, 2014

(54) MEASUREMENT OF AN ANALYTE ON THE SKIN USING A HUE ANGLE

(75) Inventor: Michael J. Evelegh, Dundas (CA)

(73) Assignee: Miraculins Inc., Winnipeg, Manitoba (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/542,125

(22) Filed: Jul. 5, 2012

(65) Prior Publication Data

US 2012/0277553 A1  Nov. 1, 2012

Related U.S. Application Data

(63) Continuation of application No. 10/887,737, filed on Jul. 9, 2004, now Pat. No. 8,236,516, which is a continuation of application No. 09/830,708, filed on Apr. 30, 2001, now abandoned.

(30) Foreign Application Priority Data

Aug. 6, 1999 (CA) .................................. 2279793
Jan. 17, 2000 (CA) .................................. 2296163
Apr. 20, 2000 (CA) .................................. 2306315

(51) Int. Cl.
*A61B 5/1455* (2006.01)
*C12Q 1/60* (2006.01)
*C12Q 1/54* (2006.01)
*A61B 5/1477* (2006.01)

(52) U.S. Cl.
USPC ................................ 600/310; 435/4; 435/11

(58) Field of Classification Search
USPC ....................................................... 435/4, 11
See application file for complete search history.

(56) References Cited

U.S. PATENT DOCUMENTS

| | | | |
|---|---|---|---|
| 4,855,228 A | 8/1989 | Charlton et al. | |
| 4,857,457 A | 8/1989 | Shamsuddin et al. | |
| 4,898,813 A | 2/1990 | Albarella et al. | |
| 5,162,202 A | 11/1992 | Shamsuddin | |
| 5,178,831 A | 1/1993 | Sakota et al. | |
| 5,179,288 A | 1/1993 | Miffitt et al. | |
| 5,348,860 A | 9/1994 | Shamsuddin | |
| 5,416,025 A | 5/1995 | Krepinsky et al. | |
| 5,489,510 A | 2/1996 | Lopukhin et al. | |
| 5,587,295 A | 12/1996 | Lopukhin et al. | |
| 5,917,541 A | 6/1999 | Nakagome et al. | |
| 6,128,516 A | 10/2000 | Macfarlane et al. | |
| 6,187,591 B1 | 2/2001 | Krepinsky et al. | |
| 6,365,363 B1 | 4/2002 | Parfenov et al. | |
| 6,574,425 B1 | 6/2003 | Weiss et al. | |
| 8,236,516 B2 * | 8/2012 | Evelegh ........................... | 435/11 |
| 2001/0007773 A1 | 7/2001 | Maleev et al. | |

FOREIGN PATENT DOCUMENTS

| | | |
|---|---|---|
| DE | 0 987 553 A1 | 3/2000 |
| EP | 0 110 173 A1 | 6/1984 |
| EP | 0 893 690 A1 | 1/1999 |
| JP | 43 31 010 A1 | 3/1998 |
| JP | 10073491 A | 3/1998 |
| RU | 2002103517 | 10/2004 |
| WO | WO 90/00251 | 1/1990 |
| WO | WO 90/11526 | 10/1990 |
| WO | WO 93/12253 | 6/1993 |
| WO | WO 95/14927 | 6/1995 |
| WO | WO 96/08710 | 3/1996 |
| WO | WO 96/40924 | 12/1996 |
| WO | WO 98/37424 | 8/1998 |
| WO | WO 01/11359 | 2/2001 |

OTHER PUBLICATIONS

CA22 Tethered Spectrophotometer; "A Precision Lightweight Spectrophotometer Designed to Take Spectral Measurements in a Tethered Mode to a PC"; published at ehsy.com/affix_pdf/pdf/2008/08/1219998783.pdf.
Weatherall, I.L. and Lee, William G.; "Instrumental evaluation of some New Zealand fruit colours using CIELAB values"; New Zealand Journal of Botany; (1991); 29: 197-205.
"A Guide to Understanding Color Communication; Communicating Color"; (2007); published at xrite.com/documents/literature/en/L10-001_Understand_Color_en.pdf.
*Principals of Color Technology*, by Fred W. Billmeyer and Max Saltzman, published by John Wiley and Sons (Chapter 1).
Titova G.V., Klyueve N.N., Kozhevnikova K.A., et al., *Biochemistry*, vol. 45, No. 1, pp. 51-55 (1980).
Katzenstein I.J., Spielvogel A.M., Norman A.W., "Stoichiometry of Interaction of the Polyene Antibiotic, Pilipin, With Free and Liposomal-Bound Cholesterol," J. Antibiot., vol. 27, No. 12, pp. 943-951 (1974).
Readio, Josephine D., et al., "Equilibrium Binding of Amphotericin B and its Methyl Ester and Borate Complex to Sterols," Biochem. Biophys. Acta, 685 (2) pp. 219-224 (1982).

(Continued)

*Primary Examiner* — Ralph Gitomer

(74) *Attorney, Agent, or Firm* — Preti Flaherty Beliveau & Pachios LLP

(57) ABSTRACT

A process is provided for analyzing a skin in any of a number of biochemical or immunological tests for an analyte which involves applying to a skin surface on a patient a reagent which selectively binds to the analyte to form an analyte-reagent complex; subjecting the skin surface on the patient to a treatment which develops a color correlating to an amount of analyte in the specimen; measuring a hue angle of the color developed on the skin surface of the patient by measuring a reflectance over a range of visible light spectrum at a plurality of intervals in wavelength of the visible light spectrum to obtain a measurement; and correlating the measurement of the hue angle to determine a concentration of the analyte.

7 Claims, 4 Drawing Sheets

(56) References Cited

OTHER PUBLICATIONS

Nikitin Y.P., Gordienko I.A., Dolgov A.V., and Filimonova T.A., "Cholesterol Content in the Skin and its Correlation with Lipid Quotient in the Serum in Normals and in Patients with Ischemica Cardiac Disease," Cardiology 1987 II, No. 10, pp. 48-51 (1987).

Klimov A.N., Titova G.V., Koznevnikova K.A., Biochemistry, vol. 47, No. 2, pp. 226-232 (1982).

Klimov, A.N., Koznevnikova K.A., Klyueva N.N. et al., Voprosy Meal., Hhimii, vol. 30, No. 3, pp. 86-90 (1984).

Hinta P.H., "Structure and biological activity of steroid glycosides of spirostan and furostan series," Hishinev, Stina, p. 142 (1987).

Deknosidze G.E., Chirva V.Y., Sergienko T.V., Uvarova N.L., "Study on Triterpene Glycosides," Tbilisi, Mesniereba (1982).

Dalin M.V., Fish N.G., "Protein toxins or Microorganisms," Moscow, Medicine (1980).

Jong Shan Shyng, Wang Hsi-Hua, Clin. J. Microbiol., 9, (1-2), pp. 19-30 (1976).

Andrew Sincock, "Computerised Laser analysis of breast sections and cervical smears by transnuclear scanning", Medical Science Research, vol. 24, No. 3, pp. 165-166 (1996).

Evelegh M J et al., "Use of Skin Cholesterol to Monitor Response to Cholesterol-Lowering Therapy", Clinical Chemistry, vol. 45, No. 6, pp. A29 (1999).

William Galbraith et al., "Colorimetry for the Stain Technologist. IV. Analysis of the Components of Color Difference", Stain Technology, vol. 60, No. 4, pp. 239-246 (1985).

M. Goto et al., "Chromaticity Analysis of Immunostained Tumor Specimens", Pathology Research and Practice, vol. 188, No. 4,5, pp. 433-437 (1992).

Billmeyer and Saltzman's Principles of Color Technology, Roy Berns ed. John Wiley & Sons NY, 2000. Chapters 1 and 2, pp. 1-53.

\* cited by examiner

MEASUREMENT OF AN ANALYTE ON THE SKIN USING A HUE ANGLE

CROSS REFERENCE TO RELATED APPLICATIONS

This application is a continuation of U.S. application Ser. No. 10/887,737 filed on Jul. 9, 2004, entitled DETERMINING CHOLESTEROL DIRECTLY ON SKIN SURFACES now U.S. Pat. No. 8,236,516, which is a continuation of U.S. application Ser. No. 09/830,708 filed on Apr. 30, 2001 now abandoned, entitled SPECTROPHOTOMETRIC MEASUREMENTS IN COLOR-BASED BIOCHEMICAL AND IMMUNOLOGICAL ASSAYS, the whole of which are hereby incorporated by reference herein. This application also claims the benefit of priority from Canadian Patent Application No. 2,306,315 filed on Apr. 20, 2000, entitled NON-INVASIVE CHOLESTEROL TEST, Canadian Patent Application No. 2,296,163 filed on Jan. 17, 2000, entitled TEST FOR CANCER, and Canadian Patent Application No. 2,279,793 filed on Aug. 6, 1999, entitled MUCOUS TEST FOR CANCER, the whole of which are hereby incorporated by reference herein.

FIELD OF THE INVENTION

This invention relates to color-based biochemical and immunological assays and tests in which an assay or test sample is subjected to spectrophotometric measurement of color characteristics, in particular, the hue angle and/or chroma. Assays using such measurements have proven useful in producing quantitative or semi-quantitative results in a wide range of medical test and screening procedures and diagnostic methods.

BACKGROUND OF THE INVENTION

As discussed in more detail below, many diagnostic tests depend on the visual examination and appraisal of a color which is developed in a sample of biological material by treatment of the sample with reagents that generate color in positive correlation with the amount of an analytes, i.e., a particular compound to be assayed (e.g., cholesterol) or specific molecular markers present in the sample indicative of a pathological condition, such as cancer.

Tests which require the visual examination and appraisal of the color changes are convenient and often adequate as a preliminary, subjective assessment for the presence of a target compound or a disease marker, but they are essentially non-quantitative.

I have found, surprisingly, that measurement of the hue angle and/or chroma, as well as related color characteristics, by reflective spectrophotometry, affords at least semi-quantitative measurement of the result of assays. From such measurement of one or more defined characteristics of the color of an assay sample derive much valuable information concerning the presence or absence of progressive diseases such as cancer, as well as their stage of development.

Color-Based Test for Cancer

From U.S. Pat. No. 5,162,202, it is known to screen rectal mucous from human patients for detection of colorectal cancer and cancers of the large intestine. The mucous is collected on a membrane filter. A cellulose membrane filter is pre-prepared by impregnation with a solution of the enzyme galactose oxidase in a phosphate buffer, and then lyophilized. At the time of use, the cellulose membrane filter is moistened and then contacted with the membrane filter carrying the mucous sample, for 1-2 hours. Then the mucous bearing membrane filter is washed and reacted with basic fuchsin for 15 minutes, washed and dried. De-colorization of the fuchsin indicates the presence of carbohydrate markers of a cancerous or pre-cancerous condition in the mucous. Such a test is lengthy and tedious to perform, and does not have a high degree of sensitivity, so that it may give false negatives.

An improved rectal mucous test is disclosed in U.S. Pat. No. 5,348,860 Shamsuddin, issued Sep. 20, 1994. In this procedure, the mucous sample is collected and immobilized on a membrane filter, and is treated with galactose oxidase to effect oxidation of any vicinal galactose moieties in the sample to vicinal aldehyde moieties. These are visualized with Schiff's Reagent. This is a more rapid procedure. Samples which test negative by this procedure can be further oxidized with periodic acid and then visualized with Schiff's Reagent, so as to reduce the chances of obtaining false negative results.

A continuing problem with known mucous tests is that the staining results need to be visually examined and appraised. Whilst such examinations are adequate as a preliminary, subjective assessment for the presence of absence of cancer markers, they are qualitative only. They do not give reliable quantitative information about the amounts and concentrations of markers which have been found, and which could give indications of the state of progression of the cancer condition, if present. Moreover, the medium on which the samples are developed, normally a cellulose membrane, such as filter paper, may itself contain compounds capable of participating in the color development reactions. This can give a "background" which complicates the interpretation of the test results, and reduces its sensitivity. This requires a trained individual skilled in the interpretation of the test result.

Color-Based Assay of Cholesterol Levels

The association of high serum cholesterol levels in patients with propensity to develop atherosclerosis and consequent increased incidence of coronary heart attack, stroke and PVD is firmly established, so that frequent monitoring of patient's cholesterol levels is desirable. More commonly, cholesterol level is determined from extracted blood samples. Many other diagnostic tests are commonly performed also on extracted blood samples, but most of these need only be conducted at longer intervals than cholesterol tests. The invasive nature of the blood collection procedure for cholesterol analysis discourages many patients from undergoing cholesterol monitoring as frequently as is advisable. Accordingly, there is a need for a non-invasive cholesterol test.

It is estimated that the skin contains about 11% of the body's total cholesterol, resulting largely from epidermal steroidogenesis and cholesterol diffusion from blood vessels. It has been postulated that the level of skin cholesterol may more accurately reflect the extent of atherosclerosis than the amount of serum cholesterol.

Nikitin, Y P, Gordenko, I. A., Dolgov, A. V. and Filimonova, T. A., "Cholesterol Content in the Skin and its Correlation with Lipid Quotient in the Serum in Normals and in Patients with Ischemic Cardiac Disease", Cardiology 1987 II, No. 10, page 48-51, and others, have demonstrated that there is a close correlation between cholesterol content in the arterial wall and cholesterol content in the skin of a patient. This suggests a possibility of developing skin tests to determine a patient's cholesterol level. The method described by Nikitin et al., however, involves removing and analyzing skin samples in vitro, a method which is impractical in a clinical setting.

U.S. Pat. Nos. 5,489,510 and 5,587,295 Lopukhin et al., describe a non-invasive diagnostic test which is performed on the surface of the patient's skin, and which indicates skin cholesterol levels. In the test described in these patents, reagents are provided in the form of affino-enzymatic compounds which are bi-functional in their nature. The bifunctional compound A-B includes a binding agent A which is capable of discriminately forming stable complexes with cholesterol of the skin in order to give the whole bi-functional compound an affinity to cholesterol (for example digitonin); and a visualizing agent B, for example an enzyme such as peroxidase, which permits detection of the bi-functional compounds bound to skin cholesterol. In the practice of this test, a complex of a binding agent A and a visualizing agent B, optionally in combination with a bridging agent C to enhance the sensitivity of the test, i.e., a bi-functional conjugate A-C-B, may be placed on the skin of the palm of the patient. Bridging agent C is suitably a high molecular weight polyfunctional compound such as a polysaccharide or a protein, and serves to space the visualizing agent from the binding agent to minimize steric hindrance of the cholesterol-binding agent reaction. After a suitable incubation period to ensure binding of the complex to the cholesterol of the skin, the area is fully rinsed with clean water to remove unbound reagents. Then the binding area is treated with indicating agent D, to react with visualizing agent B so as to develop color. The greater the cholesterol level, the greater the degree of binding of the bi-functional compound to the skin, and the greater the degree of color development.

A cholesterol test based on the aforementioned patents of Lopukhin et al. has been developed commercially and put into commercial practice. It involves the provision of a kit comprising reagents and a color chart or reader. Most of the reagents are contained in a vial, which the user applies to the test area, on the palm of the hand, after removing the protective covers. After incubation, the user applies indicating agent and visually assesses the degree of color change which occurs, alongside the color chart or using the reader.

One disadvantage of such a test is the requirement for visual assessment of the color changes. Whilst it is convenient that the test can be carried out by un-skilled personnel, such as the patient, the visual assessment of the resultant color change is subjective and essentially non-quantitative. It can give a valuable indication of cholesterol levels and hence potential problems, but not the type of quantitative measurements which a prescribing physician commonly prefers. The assessment is easily influenced by the nature and color of the background, namely the skin.

It is the general object of the present invention to provide a novel method for determining and measuring the result of a color-based biochemical or immunological assay which does not rely on subjective visual assessment. It is a further and more specific object to provide a method for the quantifiable measurement of the amount of a target compound in a sample of biological material which has been subjected to a biochemical or immunological assay that generates a color in positive correlation with the amount of said target compound.

It is also an object of the present invention to provide a novel test of body secretions, liquid and semi-solid, and a kit for use therein, useful in cancer diagnosis.

It is a further and more specific object of the present invention to provide a novel test of rectal mucous and other secretions, liquid and semi-solid, including stool, and mixtures thereof, and a kit for use therein, which overcomes or at least significantly reduces one or more of the above disadvantages. In the following description, the term "colon-contacting semi-solids" is used to denote mucus, stool and other liquids or semi-solids obtained from the rectum or colon of a patient, and mixtures thereof, which provide the analyzable material for use in the process of the present invention.

It is also an object of the present invention to provide a novel diagnostic, non-invasive test for cholesterol.

It is a further and more specific object to provide such a test for cholesterol which is capable of producing at least semi-quantitative results.

SUMMARY OF THE INVENTION

With a view to overcoming the disadvantages of prior diagnostic tests based on the requirement for visual assessment of color changes, the present invention in its broadest aspect utilizes certain specific parameters detectable with a spectrophotometer, but not previously used for the present applications. These colorimetric parameters are examined and analyzed, to provide assays and diagnoses of enhanced sensitivity and specificity. The color developed in an assay or test is measured at various wavelengths and the hue angle and/or chroma are measured to provide valuable information concerning the presence or absence of target compounds, disease states or other conditions which are the object of the color-based assay or test. In some cases, the measurement of related color characteristics, such as lightness or saturation, may improve the sensitivity of a test or assay still further.

According to another aspect of the invention, there is provided a process of diagnosing liquid or semi-solid samples of a patient's body secretions for evidence of abnormalities in the tissues or organs from which the secretions emanate, which comprises collecting a liquid or semi-solid body secretion sample from a patient, depositing at least a portion of the sample on a generally white substrate, staining the sample on the substrate and color developing the stained sample, determining a defined color characteristic of the developed color of the sample by spectrophotometry, and classifying the sample as normal or abnormal according to the value of the defined color characteristic so obtained.

According to a further aspect of the invention, there is provided a system for analysis of liquid or semi-solid body secretion samples obtained from human patients to diagnose for the presence or absence of abnormalities in the patient, by utilization of determination of a defined color characteristic developed in the sample and selected from hue angle, chroma or saturation, and lightness, said system comprising:

a white, non-cellulosic substrate with a porous "pebbled" surface, for receiving and holding the sample during development;

a source of galactose oxidase, adapted to apply galactose oxidase to the substrate surface for selective enzymatic oxidation of the sample thereon;

a source of Schiff's Reagent, adapted to apply Schiff's Reagent to the oxidized sample on the substrate for development of analyzable therein.

and means for presenting the color-developed sample to a portable reflectance spectrophotometer capable of determining and reporting a defined color characteristic selected from hue angle, chroma or saturation, and lightness from stained samples on said substrate.

According to a further, more particular aspect of the invention, there is provided a process of diagnosing rectal colon-contacting semi-solid samples for evidence of abnormalities in the source patient, which comprises collecting a colon-contacting semi-solid sample from a patient, depositing at least a portion of the sample on a generally white substrate, staining the sample on the substrate with galactose oxidase, color developing the stained sample with Schiff's Reagent, determining a defined color characteristic of the developed color of the sample by spectrophotometry, and classifying the sample as normal or abnormal according to the value of the defined color characteristic so obtained.

According to a further aspect of the invention, there is provided a kit for analysis of semi-solid colon-contacting samples obtained from human patients to diagnose for the presence or absence of rectal abnormalities in the patient, comprising;

a generally white, non-cellulosic substrate for receiving the sample;

a source of galactose oxidase;

a source of Schiff's Reagent;

and a portable reflectance spectrophotometer capable of determining and reporting a defined color characteristic selected from hue angle, chroma or saturation, and lightness from stained samples on said substrate.

According to another aspect of the invention, there is provided a test in which liquid or semi-solid reagents are applied to a patient's skin, to bind to the skin cholesterol, followed by development of color in the reagents, the degree of color development being directly related to the quantity of cholesterol in the skin. Instead of visual assessment, however, the liquid or semi solid reagents in which the color has been developed are analyzed colorimetrically, to determine degree of color development from which cholesterol levels can be at least semi-quantitatively obtained. The chosen colorimetric parameters, such as hue angle or shade, are independent of color density, intensity or lightness (L), and simply measure the color shade. This essentially eliminates the uncertainties introduced from the background color of the skin, so that the test can be conducted on the patient's skin surface. Instrumental colorimetric (spectrophotometric) analysis produces objective numbers which are at least semi-quantitative and indicative of cholesterol levels of the patient.

According to the present invention, in a still further aspect there is provided a process of determining skin cholesterol levels of a patient, which comprises:

applying to a person's skin surface a reagent which selectively binds to skin cholesterol;

causing color developing chemical reaction with the skin cholesterol-bound reagent combination so formed, to form a colored complex;

and subjecting the colored complex so formed to spectrophotometric analysis to read therefrom a pre-defined characteristic of the color of the colored complex.

A still further aspect of the invention is a kit for determination of skin cholesterol levels of a human patient, and comprising:

a source of detecting agent, capable of binding to skin cholesterol of the patient to form a bound combination therewith on the skin;

a source of visualizing agent, capable of reacting with the detecting agent—binding agent bound combination to form an optically altered complex therewith;

a source of developing agent and means for applying the developing agent to the optically altered complex, to develop color therein;

and means for confining and for presenting said optically altered complex to a portable reflectance spectrophotometer to determine therefrom a defined color characteristic selected from hue angle, chroma or saturation.

BRIEF REFERENCE TO THE DRAWINGS

In the description of preferred embodiment of the invention which follows, that portion relating to the aforementioned aspect of the invention relating to a process and a kit for determining skin cholesterol levels of a patient, reference is made to the drawing figures, in which.

DESCRIPTION OF THE PREFERRED EMBODIMENTS

Figure 1:
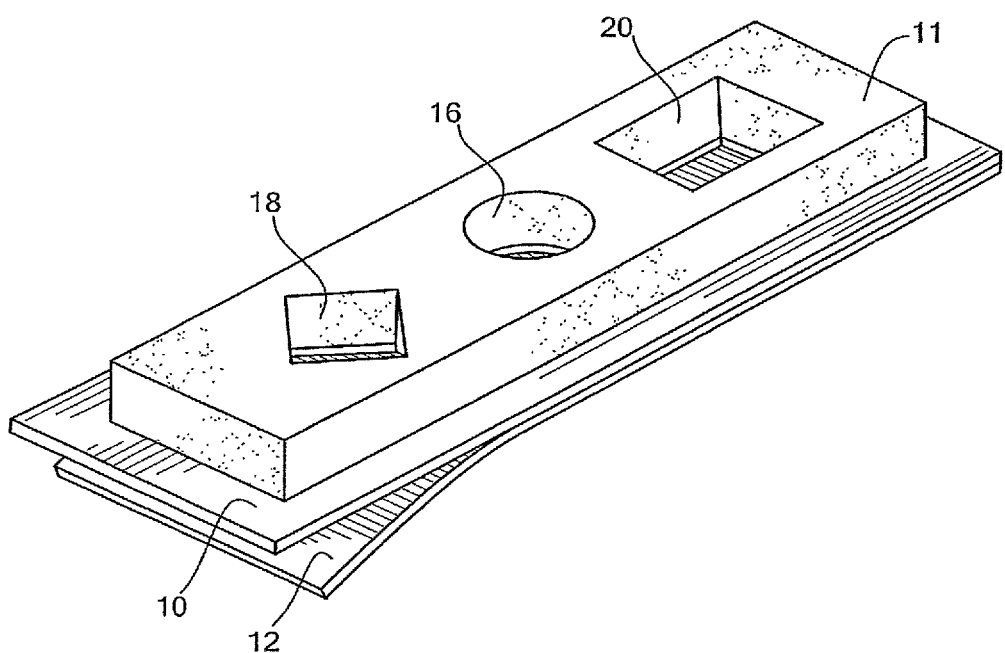
FIG. 1 is a diagrammatic illustration of a test strip for use in determining the skin cholesterol levels of a patient according to the present invention.

As evident from the foregoing discussion, applicant's basic invention of using colorimetric measurements, particularly of chroma and/or hue angle for measurement of the results of color-based assays and tests finds application in a number of aspects and embodiments. Two aspects of the invention and the preferred embodiments thereof will therefore be described further below, separately under individual headings.

Suitable spectrophotometrics for use in all aspects of the present invention are portable, reflectance-based, and give accurate measurements of color characteristics such as hue angles, lightness and chroma or saturation, when the incident light of the spectrophotometer is reflected back from the stained sample to the instrument's receiver. They are commercially available. A specific example of a suitable such instrument is that marketed by X-Rite, Grand Falls, Mich., U.S.A. as "Model CA22 Spectrophotometer". It is supplied with appropriate software so that it can be connected to a computer to give an accurate read-out of the hue angle of the stained sample under test. The spectrophotometer receives reflectances over the approximate wavelength 400-700 nm, i.e., over most of the visible light spectrum, suitably over about 20 nm intervals.

It is known that color may be defined and expressed in terms of hue angle. The concept of "hue angle" is defined and discussed in standard textbooks such as "Principles of Color Technology," by Fred W. Billmeyer and Max Saltzman, published by John Wiley and Sons (see particularly Chapters 1 and 2), incorporated herein by reference. "Hue" is the color or shade of a specimen independent of its brightness or intensity, and "hue angle" of a color or shade is the definition of its reflectance wavelength by angular position with reference to a standard three dimensional ellipsoidal continuum plot of the entire spectrum of visible light. The visible light (color) continuum is represented on an angular scale from 0 to 360°, and the angular values as read by the reflectance spectrophotometer are transformed into linearized form to give the transformed "hue angle" used in the process of the present invention.

(i) Test for Cancer

It has been surprisingly found, in accordance with the invention, that the presence of a whole range of pathologies, included bowel pathologies, lung pathologies, cervical pathologies and others, can be determined by determining the hue angle or other defined color characteristic mentioned above, of the color developed from a liquid or semi-solid body secretion from the appropriate tissue or body organ. Reaction and spectrophotometric analysis of rectal mucus, will serve to diagnose colon cancer. Thus, individuals with rectal cancer give rectal mucus samples which after staining and color developing as described, have higher hue angle numbers than those with normal bowels. Thus the hue angle or other defined color characteristic of the stained sample can be used to differentiate individuals with cancerous lesions of the bowel from those without such lesions. More specifically, samples from cancerous lesions have been found to give hue angles generally in the range 375-425°, the top quartile of measurement from clinical samples. Further, because the test result is interpreted by the portable spectrophotometer, there is no requirement that the test results be produced by a skilled, trained individual.

In a similar manner, lung cancer and lung pre-cancerous conditions can be diagnosed by subjecting lung mucus or sputum to similar color development and spectrophotometric analysis. Cervical cancer and pre-cancer can be diagnosed by such procedures applied to cervical mucus. Seminal secretions such as semen can be similarly analyzed, for cancer of the reproductive organs such as testicular cancer. Mucus of the throat can be similarly analyzed for detection and diagnosis of throat cancer. Mucus of the throat and the lungs can be obtained by known procedures, such as bronchoscopy or bronchio-alveolar washings. Breast nipple aspirate is a body fluid which can similarly be analyzed by the method of the invention, in testing for breast cancer.

A significant aspect of the preferred embodiments of the present invention is the use of a porous glass fiber membrane on which the sample is oxidized and color developed. Such a glass fiber material is essentially free from stain-producing residues, so that it presents no residues which will undergo enzymatic oxidation so as to participate in the subsequent color developing reaction. Accordingly, background color development likely to confuse or interfere with the diagnostic tests, is effectively eliminated. Moreover, the membrane is essentially pure white in color, further reducing background "noise" against which the results are read.

A further characteristic of the glass fiber membrane used in this aspect of the invention is its surface porosity, which allows additional spreading of the mucus sample thereon so as to expose additional carbohydrate markers in the sample to participate in the oxidation and color development reactions, with consequent improved sensitivity of test method.

A specific, preferred example of a glass fiber porous membrane for use in the present invention is that available commercially from Whatman Inc, Laboratory Division under the designation "Whatman 934-AH Glass Microfiber Filter", a borosilicate glass filter medium having high loading capacity and high retention efficiency at high flow rates. It is recommended for use in cell harvesting and liquid scintillation counting techniques. This is, however, exemplary only, and other, substantially pure white glass fibre, carbohydrate free substrates of surface porosity suitable to effect surface spreading of the colon-contacting semi-solid sample can also be used.

In a specific procedure using a preferred aspect of the present invention, as applied to colon cancer detection and using an enzymatic oxidation reaction for color development, first the sample to be tested is obtained from the patient. Lubricant is supplied to the gloved finger of the operator. The finger is inserted into the rectum of the patient and rotated 360° to obtain a representative sample of colon-contacting semi-solid such as rectal mucus. The finger is removed from the rectum and the sample is smeared onto the surface of the white membrane filter described above, mounted on a rectal mucus test card with appropriate covering, protection and identification, and the card is analyzed.

For analysis, the backing is removed from the rectal mucus test card, and 50 µL of standard galactose oxidase solution is added to the test card. Incubation proceeds, in the standard way, for 10 minutes. Then the card is dipped into double distilled water for 30 seconds and then 1 mL of Schiff's Reagent is applied, for 3 minutes. The color is then developed by transferring the card through four water rinses for 10 minutes each rinse. The card is allowed to dry, and the score is determined by reading the hue angle with the portable spectrophotometer, of the type previously described. A score of hue angle below a certain predetermined value (350 in the case of rectal mucus samples) indicate a normal, healthy tissue origin. Scores over a certain predetermined value (370 in the case of rectal mucus) indicate a cancerous tissue origin.

Samples giving intermediate values may be subjected to universal oxidation to assist in final diagnosis. Based on the knowledge that, in any sample, only a proportion of the vicinal hydroxyl groups on the carbohydrate marker will have enzymatically oxidized to develop color, one can subsequently oxidize all of the remaining such groups with a powerful oxidizing agent such as periodate, and then redevelop the color and test for it. If this makes a large difference in comparison with the original result, it indicates that the sample should be classified as if it had given a higher result initially. If it makes only a minor difference, or no significant difference, the sample can be more safely grouped with those giving the lower results.

From the values of hue angle simply read out of the spectrophotometer in this way, the operator can, without any subjective interpretation, determine whether the sample originates with a patient having healthy, normal colon or cancerous colon, with greatly reduced chances of false positive or false negative readings, as compared with prior diagnostic methods. The same standard collection, staining, incubation and color development steps are taken, and the same standard reagents are used, so that the new procedure according to the invention can be adopted by established diagnostic laboratories with minimum disruption and economic expenditure.

Essentially similar procedures are adopted in respect of other mucus samples from other body organs and tissues. Enzymatic oxidation with galactose oxidase, followed by reaction with Schiff's Reagent, is preferred as the color developing reaction procedure for subsequent color analysis according to the invention. However, the invention is not limited thereto. Any procedure which will result in selective reaction resulting in color development characteristic of the cancer development thereof, can be employed. For example, direct reaction of the sample with Schiff's Reagent, without an enzymatic reaction step, can be used for color development. In all cases the spectrophotometric analysis of the developed color to determine an objective parameter of the shade or hue of the color, e.g., hue angle constitutes the use of the present invention, such color parameters having been found to correlate with the presence and the extent of progression of various cancers.

(ii) Non-Invasive Cholesterol Test

The preferred process of this aspect of the invention employs liquid or semi-solid biochemical reagents, develops color therein determinative of the patient's skin cholesterol content, and subjects the color so developed to spectrophotometric analysis. According to the invention, the precise nature and identity or shade of the color so developed, as characterized for example by its hue angle, correlates with the amount of bound complex formed and hence with the cholesterol content of the skin. This measurement of color characteristic is objective and at least semi-quantitative. Accordingly, it is read independently of background skin color and is not influenced thereby, to any significant extent.

It is usually convenient to add all the reagents, in the appropriate order, to the patient's skin surface, allow color development on the skin surface, and then examine the color-developed complex spectrophotometrically, while it remains on the skin. The entire test can be conducted in under five minutes. The area of skin chosen for the test should be one which is essentially free from sebaceous glands, since such glands contribute cholesterol-containing sebum which would interfere with the results. The sole of the foot and the palm of the hand are suitable such skin areas, with the palm of the hand being the most convenient for use in the present test.

The kit includes a means for confining and presenting the color-developed complex for analysis by a portable spectrophotometer. Suitably this is a container in the form of a skin-adherent strip, with one or more wells passing therethrough, so that reagents contained in the wells can contact the patient's skin. Container design will largely be dictated by the physical characteristics of the spectrophotometer. Instead of a container for the reagents, an inert thixotropic agent can be included with the reagents, to limit their spread across the skin surface and to prevent the mixing of test reagents with control reagents applied to adjacent skin locations.

As with other color-based tests and assays to which the present invention is applicable, it is a feature of the non-invasive cholesterol test according to this aspect of the invention that the hue angle of the colored complex bound to the skin cholesterol correlates with skin cholesterol content.

Suitable chemical reagents for use according to this aspect of the intention are generally those described in the aforementioned Lopukhin et al. patents, the disclosures of which are incorporated herein by reference. Their precise choice is not an essential or limiting feature of the present invention, provided that their use in combination with one another results in the chemical development of color as a result of binding to skin cholesterol. The term "binding" is used herein in its broad sense of chemical reaction to cause attachment of one chemical entity to another, as well as specific affinity-type "gripping" interaction often encountered in biochemical systems.

Thus, the binding agent A is selected from a group of substances capable of discriminately forming stable complexes with free cholesterol of the skin in order to give the whole bi-functional compound in which it is involved an affinity to cholesterol. It can form a stable complex by direct reaction with cholesterol, before or after it is chemically attached to the visualizing agent B directly or through the bridging agent C.

Representative classes of compounds suitable as cholesterol binding agents A include:

steroid glycosides, containing as an aglycone a cyclopentaneperhydrophenanthrene fragment of the furostanole or spirostanole series, and an oligosaccharide fragment including 3 to 10 monosaccharide residues with linear or branched structures (Hinta P. H. "Structure and biological activity of steroid glycosides of spirostan and furostan series", Hishinev, Stinza, 1987, pg. 142) specific preferred examples of which are funcosides C, D, E, F, G and I, dioscin, rocosides C, D and E, lanotigonine, digitonin and tomatine;

triterpene glycosides, containing an aglycone of alpha or beta-amyryl, lupane, hopane, dommarane, linostane or holostane series, and oligosaccharides comprising saccharide residues of branched or linear structure (Deknnosidze G. E., Chirva V. Y., Sergienko T. V., Uvarova N. L. "Study on Triterpene Glycosides", Tbilisi, Mesniereba, 1982;

hydrophobic proteins capable of discriminately forming a complex compound with cholesterol (Himov A. N., Titova G. V., Kozhevnikov H. A., Biochemistry, 1982, Vol. 47, No. 2, pg. 226-232); Himov A. N., Hozhevnikov H. A., Klyueva N. N. et al. Voprosy Meal., Hhimii, 1984, Vol. 30, No. 3, p. 86-90; Titova G. V., Hilyueva N. N., Hozhevnikov H. A., et al. Biochemistry, 1980, Vol. 45, No. 1, pg 51-55);

protein toxins, capable of discriminately forming complex compounds with cholesterol. They are obtained from bacteria, marine microorganisms, insects of snakes (Dalin M. V., Fish N. G. "Protein Toxins or Microorganisms", Moscow, Medicine, 1980); or polyens antibiotics, capable of discriminately forming complex compounds with cholesterol (I. J. Katzenstein, A. M. Spielvogel, A. W. Norman, J. Antibiot., 27, 12, 1974, pg. 943-951; Jong Shan Shyng, Wang Hsi-Hua, Clin. J. Microbiol., 1976, 9, (1-2), pg. 19-30; Readio Josphine D. et al. Biochim. Biophys. Acta, 1982, 685 (2), pg 219-24); or high affinity enzymes, whose substrate is cholesterol, and which have a high affinity to it. All of the above-mentioned publications are incorporated herein by reference.

The most preferred choice for cholesterol binding agent A is digitonin.

Visualizing agent B is commonly an enzyme, since enzyme/substrate reactions resulting in a color change are particularly useful. Specific examples of suitable such enzymes include acetyl choline sterase, tyrosinase, glucose-6-phosphate dehydrogenase, glucose oxidase, glucoamylase, beta-D-galactosidase, peroxidase, alkaline or acid phosphatase, alpha-chymotrypsin, and pyrophosphatase. Peroxidase is a preferred choice e.g., horseradish peroxidase (HRP).

The use of a bridging agent C enhances the technical performance of the method, and facilitates the production of the resulting, desirable A-C-B complex from which color can be developed, whilst preserving the functional activity of agents A and B. The most preferred A-C-B complexes are those which use steroid glycosides, which contain as an aglycone, a cyclopentaneperhydrophenanthrene fragment from the furostanol or spirostanol series and oligosaccharide fragments including two to 10 monosaccharides residues with linear or branched structures such as digitonin as the cholesterol affinity binding agent A. It is particularly desirable to use a bridging agent C when digitonin is chosen as the cholesterol binding agent A and HRP is chosen as the visualizing agent, since HRP is a relatively large molecule which, if bound directly to digitonin, might sterically hinder the reaction of digitonin with skin cholesterol. As bridging agent C for such purposes, it is preferred to use high molecular weight polyfunctional compounds. Their use allows a wide range of control over the proportion of agents A and C in the final complex. Such high molecular weight polyfunctional bridging agents C may be various polysaccharides, proteins or synthetic polymers, i.e., any suitable high molecular weight compound containing primary amine, carboxyl, hydroxyl, aldehyde, haloidanhydride, mixed anhydride, iminoester, azide, hydroxide, maleimide, isocyanate, or epoxide functional groups. Copolymers of acrylic acid or maleic acid or maleic anhydride and N-vinylpyrrolidone are the most preferred high molecular weight polyfunctional bridging agents C. Asymmetric low molecular weight bi-functional compounds such as bromocyan, trichlorotriazine or 2-amino-4,6-dichloro-3-triazine can also be used.

Indicating agent D typically contains a substrate of the enzyme employed as the visualizing agent B, and additional compounds needed to make the reaction between the enzyme and its substrate visible. A specific example of such an indicator agent D, for use with peroxidase enzyme as visualizing agent B, is an agent containing hydrogen peroxide, N,N-diethyl-p-phenylidene sulfate, together with appropriate stabilizers. Indicator agent D is selected in combination with visualizing agent B, from the range of compounds known in the art which will generate color developing reactions in combination with the chosen enzyme.

For conducting the test according to the invention, a kit is provided. The kit includes the required reagents in appropriately sealed packages such as vials or bottles equipped with droppers, a container or other confining means in which the color developing reactions can be conducted, on the patient's skin, whilst preventing spread of the reagents over too wide an area, and from which developed color can be presented to a means for determining and reporting a defined colored characteristic such as hue angle, e.g., a portable reflectance spectrometer, for examination and measurement. The container is suitably an adhesive strip provided with one or more cutout wells, initially provided with a protective backing to protect the adhesive. Preferably the container has at least two or three wells, so that control experiments can be conducted alongside test experiments. To facilitate the correct conducting of the test experiments and controlled experiments, the wells are conveniently made visually distinct from one another, e.g., of different shapes.

FIG. 1 of the accompanying drawings illustrates such a container for use in the present invention, in the form of a test strip 10, of rectangular shape. The strip comprises a foam pad 11, with a layer of skin compatible adhesive (not shown) temporarily protected by a peelable release sheet (not shown). A first central well 16 for test purposes, of circular cross-section, extend through the foam body of the strip, and through the adhesive layer 12. A second well 18, for positive control purposes, of diamond cross-section, and a third well 20, for negative control purposes, of square cross-section, are similarly provided in the foam body of the strip 10, flanking the central well 16. The different visual shapes of the wells assist the operator in conducting the tests, by aiding the correct choice of well for its respective purposes.

The test is conducted preferably on the skin of the palm of the patient's hand. The container for the reagents, in the form of an adhesive strip, is temporarily adhered to the skin so that the open bottom of the wells contact the skin. Reagents are dropped into the wells, the color is developed in the wells, and then the color is read by the spectrophotometer without removing the strip from the skin. For this purpose, a specially designed spectrophotometer, constituting another feature of the invention, is used. The spectrophotometer transmits readings to a computer for analysis. The spectrophotometer is designed to ensure proper alignment over the test cell.

Accordingly, this aspect of the invention provides a spectrophotometer adapted to transmit signals from reading color reflectance of a test sample to a computer, the spectrophotometer having a body, a light emitting means in said body, an apertured lower portion of said body through which light emitting means may be directed to shine light, and a recess in the lower surface of said lower portion, adapted to fit over the welled test strip applied to a patient's skin surface to provide precise registry of the spectrophotometer and the test sample in a well of said welled test strip. Preferably, the lower portion of the spectrophotometer is hinged to the body, so that it can be conveniently fitted into proper registry with the test strip while in the open position, and then closed to the body of the spectrophotometer for taking measurements. Preferably also, the hinged lower portion and the body of the spectrophotometer are provided with electrical contacts to act as a switch, to turn on the light of the spectrophotometer when the lower portion is closed to the body of the spectrophotometer.

Figure 2:
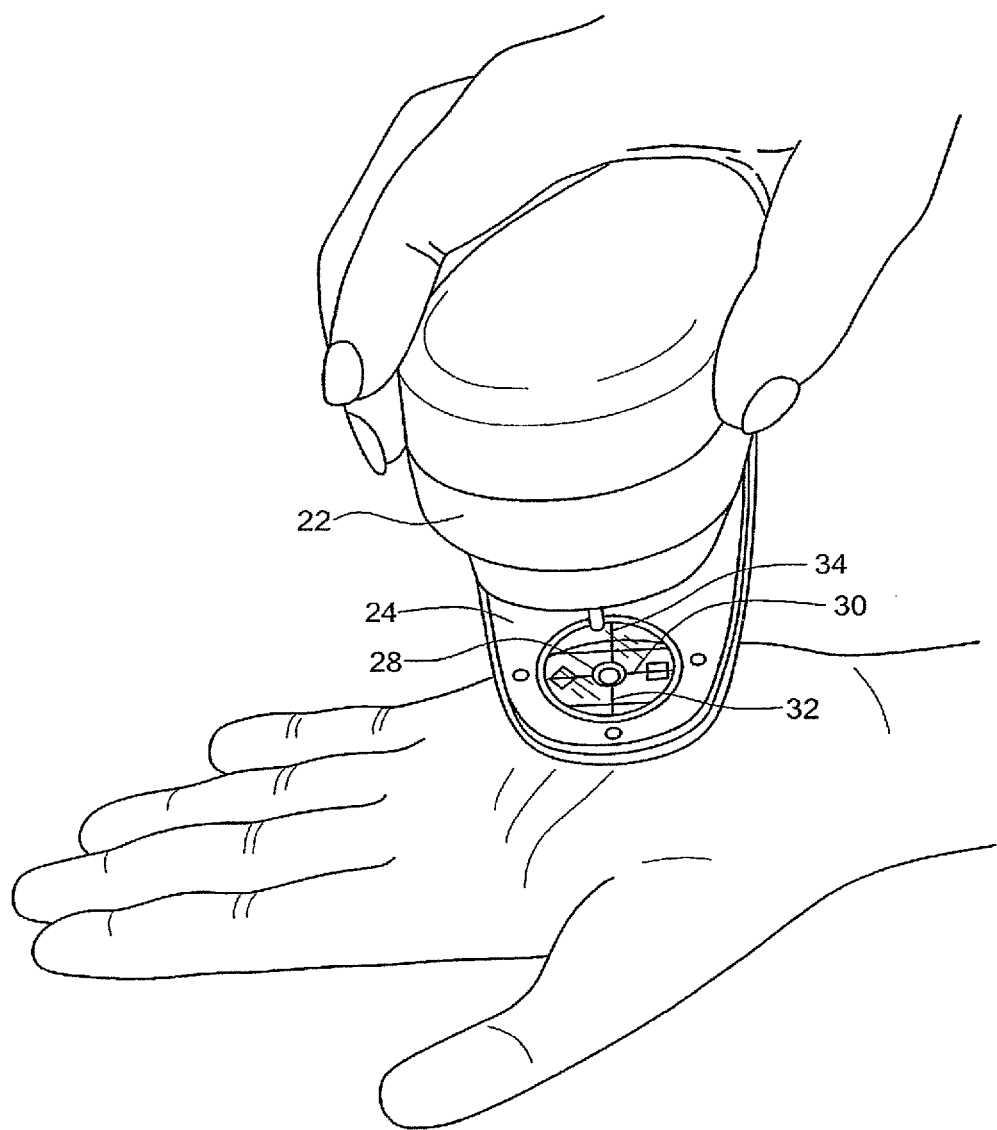
FIG. 2 is an illustration of a spectrophotometer reader in use in measuring skin cholesterol levels according to the present invention, and in its open position.
Figure 3:
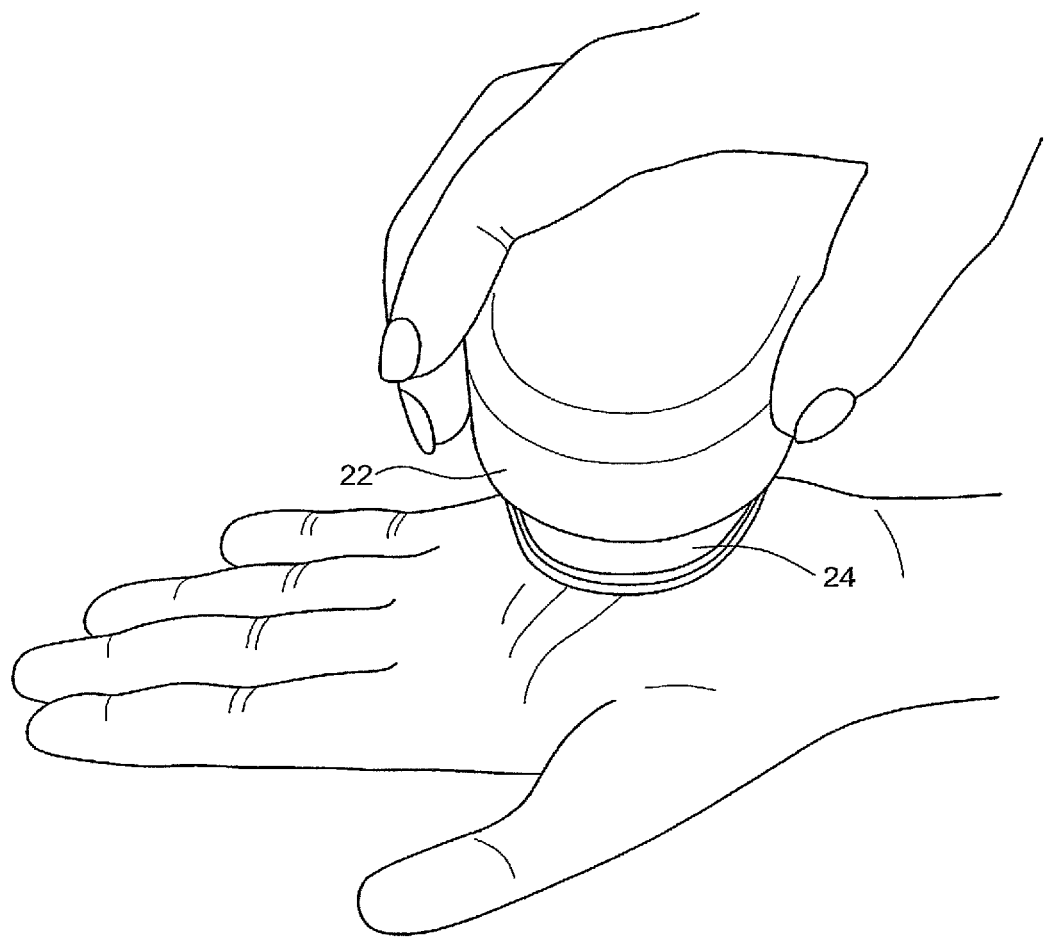
FIG. 3 is a view similar to FIG. 2, but with the spectrophotometer in the closed position.
Figure 4:
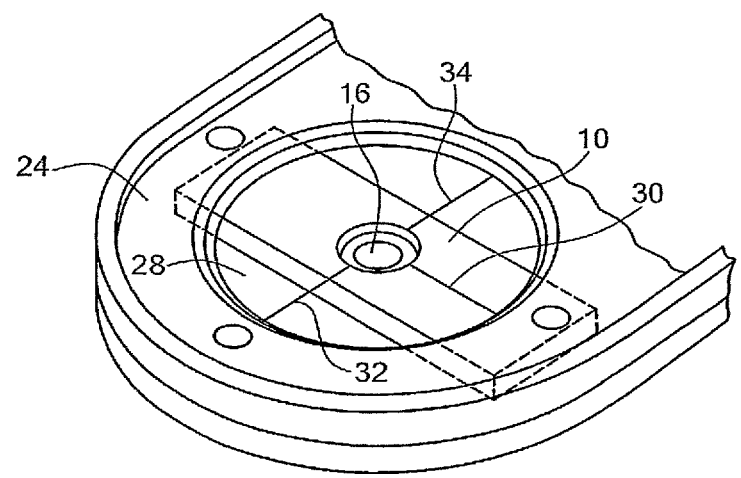
FIG. 4 is a detail view of the lower portion or shoe of the spectrophotometer shown in FIG. 2 and FIG. 3.

FIGS. 2, 3 and 4 of the accompanying drawings diagrammatically illustrate the spectrophotometer. It has a body 22, with electrical connection (not shown) to an appropriately programmed computer for analysis of the results read by the reader. A lower portion 24 is provided, hingedly connected (not shown) to the body 22. The lower portion 24 is apertured at 28. A groove 30 extend across the width of the undersurface of the lower portion 24, projecting upwardly from the lower most surface. The groove is closed at one side of the lower portion. The width of the groove 30 is designed to be a precise, tight fit over the test strip 10 shown in FIG. 4. An end of test strip 10 is brought into registry with the closed end of the groove, when a reading is to be taken, and this, combined with the fit of the test strip within the width of groove 30, provides precise registry of the test well 16 with the beam of light to be emitted from the body 22 of the reader, through the aperture 28. The spectrophotometer contains appropriate detector means for picking up reflectance signals from the sample in the well 16, and transmitting them for analysis and read out by the computer. The body 22 and the lower portion 24 are provided with respective electrical contacts 32, 34 which close as a switch when the lower portion 24 is closed to the body 22, thereby switching on the light for taking a measurement.

A specific test procedure will now be described, by way of specific, but non-limiting, example of the practice of the diagnostic test of the present invention.

The kit components include a dropper bottle containing detector solution (digitonin horseradish peroxidase conjugate in an aqueous buffered solution with less than 0.01% of bromonitrodioxane and methylisothiazolone as preservatives, 1.5 mL), with a distinctive colored cap (green); a dropper bottle of more highly concentrated detector reagent solution, similarly buffered and preserved with less than 0.01% bromonitrodioxane and methylisothiazolone containing to act as a positive control (1.5 ml), and with a distinctive cap (red); an indicator dropper bottle containing a solution of reagents (4.0 mL of 3,3',5,5'-tetramethylbenzidine, TMD,—hydrogen peroxide solution with 5% N,N-dimethylformamide as preservative) to react with the detector and PC reagents that are bound to skin cholesterol, to produce a blue-green color, being equipped with a distinctive cap (blue); foam pads as illustrated in FIG. 1, to which the reagents may be added, alcohol swabs and appropriate directions for use. The chemical reagents are storage stable in a refrigerator at 2-8° C. for extended periods. The system also includes a spectrophotometer as illustrated in FIGS. 2 and 3, connected to an appropriately programmed computer, and a calibration plaque for use with the spectrophotometer. The kit as supplied does not include a spectrophotometer, except perhaps when initially sold, the same spectrophotometer being re-used with subsequent "refill" kits.

Initially, the spectrophotometer is appropriately calibrated by inserting the calibration plaque into the jaws thereof, and closing it to illuminate the calibration plaque to feed calibration readings back to the spectrophotometer and computer. A signal is eventually received that calibration has been successfully completed.

The patient's hand is washed and rinsed thoroughly with soap and water and well dried. An outside portion of the palm of the patient's hand is then thoroughly cleaned with an alcohol swab, with sufficient scrub pressure to ensure thorough cleanliness. After allowing the hand to dry, release sheet 14 is removed from a test strip 10, which is then adhesively applied to the cleaned skin area of the patient's palm. The patient inverts the hand on a paper towel placed on a tabletop, and firmly pressed down to ensure that the pad is properly adhered to the palm.

Next, the reagents are added to the respective reagent wells. One drop (42 μl) of detector solution is added to round test well 16, one drop of positive control solution is added to diamond-shaped cross-section well 18, but no liquid is added to the third, square well 20 at this point. Incubation of the added solutions is allowed to proceed for 1 minute, whilst the patient holds the test hand stationery. The patient then inverts the palm, and presses the foam pad on paper towel to remove liquid from the wells. Visual inspection is undertaken to ensure that the pad and the test wells are completely dry. Then the patient rests the hand on a flat surface with the palm facing upwards.

Next, one drop of indicator is added to all three wells, including the square well previously unused, and reaction is allowed to proceed for 2 minutes, whilst the patient holds the hand stationery. Immediately afterwards, the reader 22 is put into position over test well 16, closed and a reading is taken of the color developed in the test well, transmitted to the spectrophotometer and analyzed by the computer, to give a read out of a value of hue angle.

Visual inspection of the positive control well 18 and the negative control well 20 is undertaken. If the liquid from the negative control well is colorless, and the liquid from the positive control well is colored, the test is valid. No quantitative measurements are taken of the color developed in the positive control. This is color developed from a very high solution concentration of reagent, to give a color with even very small amounts of cholesterol on the skin, and is simply indicative of the potency of the reagents, etc., for control purposes.

The residual liquid from the test strip is discarded, and the test strip is removed from the palm of the hand, followed by cleaning of the palm of the hand with an alcohol swab.

The spectrophotometer used in the present preferably measures absorbance of reflected light from the test sample, and converts it through a suitable algorithm to a value of hue angle. In the specific case of the development of color from horseradish peroxidase—TMD reaction described above, absorption at 450 nm, $A_{450nm}$, is a suitable measurement. Optical density of the absorbance at 450 nm has been experimentally determined to relate to hue angle through the relationship:

$$h° \text{ (degrees)} = 490.45 \times A_{450\,nm} + 57.124$$

This relationship is determined by measuring optical density from a series of serially diluted reaction samples at 450 nm, measuring the hue angle of the same samples, and plotting the results on a regression curve to determine the relationship. Similar relationships can be worked out experimentally in the same way for other chosen color developing tests using different enzyme—substrate pairs which develop different colors, to allow optical density recordings to be transformed into hue angle determinations.

Although specific diagnostic tests and kits for carrying them out have been described above, one of ordinary skill will appreciate that a large number of color-based assays and analyses could take advantage of the novel measurements based on hue angle or chroma disclosed herein, for example:

(i) quantification of the outcome of solid phase immunoassays such as dot blots, immunochromatographic tests and flow-through tests (sample added to a membrane with a wicking device behind it, the target analyte being then trapped and identified by the addition of a labeled detector, such as antibody tagged with enzyme or gold;

(ii) quantification of microparticle-based assays using colored beads;

(iii) as an alternative to densitometry in the analysis of stained gels;

(iv) for the quantification of Western blot analysis.

The method of the invention affords a simple approach to quantifying such results and thus supplementing information gathered from the assay to permit the application of more sophisticated techniques of statistical analysis to the test results.

Accordingly, variations to the invention are not to be regarded as a departure from the spirit and scope thereof, and all such modifications as would be obvious to one skilled in the art are intended to be included in the scope of the following claims.

What is claimed is:

1. A process of analyzing a skin for an analyte comprising the steps of:
    applying to a skin surface on a patient a reagent which selectively binds to the analyte to form an analyte-reagent complex;
    subjecting the skin surface on the patient to a treatment which develops a color on the skin surface of the patient correlating to an amount of the analyte;
    measuring a hue angle of the color developed on the patient by measuring a reflectance over a range of a visible light spectrum at a plurality of intervals in wavelength of the visible light spectrum to obtain a measurement; and
    correlating the measurement of the hue angle to determine a concentration of the analyte.

2. The process according to claim 1 wherein the reagent is a biochemical or an immunological reagent.

3. The process according to claim 1 wherein the reagent which selectively binds to the analyte is selected from the group consisting of a hydrophobic protein, a protein toxin, an antibody, and an enzyme whose substrate is the analyte.

4. The process as claimed in claim 1, further comprising treating the reagent on the skin surface with a visualizing agent.

5. The process as claimed in claim 4, further comprising treating the reagent on the skin surface with an indicating agent.

6. The process according to claim 1, wherein the visible light spectrum has a range of about 400-700 nm.

7. The process according to claim 1, wherein the intervals are each about 20 nm.

* * * * *